(12) United States Patent
Canter et al.

(10) Patent No.: US 6,750,007 B2
(45) Date of Patent: Jun. 15, 2004

(54) DEHYDRATION DETECTION DEVICE AND METHOD OF USE

(76) Inventors: Nelson Canter, 6 Tam O-Shanter Dr., Purchase, NY (US) 10577; Susan Pannullo, 25 Ackerman Rd., Saddle River, NJ (US) 07458

( * ) Notice: Subject to any disclaimer, the term of this patent is extended or adjusted under 35 U.S.C. 154(b) by 80 days.

(21) Appl. No.: 10/092,656

(22) Filed: Mar. 6, 2002

(65) Prior Publication Data

US 2003/0170607 A1 Sep. 11, 2003

(51) Int. Cl.[7] ............................ C12Q 1/00; G01N 33/53
(52) U.S. Cl. ......................................... 435/4; 435/970
(58) Field of Search ..................... 435/4, 283.1, 287.1, 435/970

(56) References Cited

U.S. PATENT DOCUMENTS

| 4,318,709 A | * | 3/1982 | Falb et al. ............... 23/230 |
| 5,403,744 A | * | 4/1995 | Zimmerle ................ 436/2 |

* cited by examiner

*Primary Examiner*—Louise N. Leary

(57) ABSTRACT

A hand-held device is provide for the self-determination of the dehydration state of a human engaged in activities causing dehydration and which might not be evident to such person. The device can be in the shape of a dipstick having one end thereof containing a chemical indicator which when contacted with a stream of urine will provide a color change corresponding to the specific gravity of the urine specimen and is indicative of the whether the person is dehydrated or not. The cap or cover or the dipstick itself contains a color chart for comparison with the color resulting from the reaction of the urine and the chemical indicator.

16 Claims, 2 Drawing Sheets

DEHYDRATION DETECTION DEVICE AND METHOD OF USE

BACKGROUND OF THE INVENTION

1) Field of the Invention

This invention relates to a device for detecting dehydration in a person and a method of use.

2) Background Art

Prior to the present invention it was not possible to quickly and adequately determine whether a person was dehydrated, particularly, if such a person was or had been engaged in some degree of physical activity and/or exposed to a hot environment for an extended period of time. In recent years several incidents have been reported in the media where otherwise healthy individuals have become so dehydrated that they collapsed, were hospitalized and in some instances died.

Urine specific is a measure of a person's level of hydration. When a person is adequately hydrated, the urine specific gravity is in the low range. When a person is dehydrated the urine specific gravity will become higher.

Urine specific gravity is often tested in hospitals and doctor's offices, generally on a sample of urine provided by the patient in a paper cup. Historically, urine specific gravity has been determined with a urinometer, which is a bulb-shaped instrument floated in a test tube of urine, a refractometer, which is a telescopic device providing an estimate of light velocity through a glass enclosed urine drop, and with a multiple-test dipstick The multiple-test dipstick has several separate reagent areas that turn different colors in response to varying levels of substances in urine, such as, glucose, protein, blood and the like. The dipstick method is the most widely used method for urine testing in the hospital or in a medical environment The specific gravity of urine is one determination which can be determined by use of the multiple-dipstick. One of the reagents on the multiple dip-stick is capable of detecting whether the urine is dilute which is an indication of normal hydration or whether it is highly concentrated which is an indication of dehydration.

In its multiple reagent form, the dipstick provides much information that is unnecessary for the simple evaluation of hydration status. The small size and cluttered layout of the multiple dipstick reagents make them difficult to read and interpret In addition the process of urinating into a cup and dipping something into the urine, followed by discarding the specimen, is awkward, messy and unsanitary. Finally, "the reading" of the test results from the dipstick must be interpreted at a single location (the bottle on which the result legend is illustrated), one at a time.

It is therefore an object of this invention to provide a single simple effective device for the determination of the immediate hydration condition in a human Another object of the invention is to provide a method for the determination of dehydration in a human. A still further object is to provide a device which is portable and simple to use. Another object is to provide a device which can provide an immediate indication or measure of the hydration status of a person in privacy and without the need or embarrassment of providing a specimen to another person. These and other objects will readily become apparent to those of ordinary skill in the light of the teachings herein set forth.

SUMMARY OF THE INVENTION

In its broad aspect, this invention is directed to a compact, portable, and effective, hand-held device for the self-determination of the dehydration status of a human.

The device is comprised of an elongated member having:

(a) (a) at a first portion thereof, a zone containing at least one chemical reagent, which when contacted with a specimen of human urine exhibits a different, specific color corresponding to whether the specific gravity of urine is within the individual ranges of:
  (i) (i) less than about 1.015
  (ii) (ii) between about 1.015 and about 1.025
  (iii) (iii) greater than about 1.025

(b) at a second portion thereof, a zone of predetermined separate colors affixed thereto, each color indicating an individual specific gravity range and therefore the hydration status of the human being tested, and wherein the device is so configured that a person can hold the device and urinate directly onto the first portion thereof without urine contacting the remainder of the device, and wherein a color change of the chemical reagent produced by contact with urine can be immediately and privately compared with the colors affixed to the cap, or cover handle of the elongated member.

DESCRIPTION OF THE PREFERRED EMBODIMENTS

The device of the present invention has been designed to test a single, relevant parameter, i.e. specific gravity, in a manner that overcomes the limitations of the multiple-dipstick method and facilitates the immediate hydration status of a human outside of the hospital or medical setting. First, only one reagent is necessary to test urine specific gravity, thus the stick contains only one reagent. With only one reagent, the test area is much larger and easier to read. Second, the design of the device avoids the need to urinate into a container. The test stick is simply held in a urine stream during the normal urination process. The reagent turns color when contacted with urine. The handle of the device, which is preferably made of plastic, prevents contact with urine. Third, the testing system is self-contained and hence can be used in privacy since the results can be read immediately from the legend on the cover cap or handle of the device. The device of the present invention is therefore completely portable and readable on the spot since no remote interpretation is necessary. Also and infinite number of test sticks can be read simultaneously.

Figure 1:
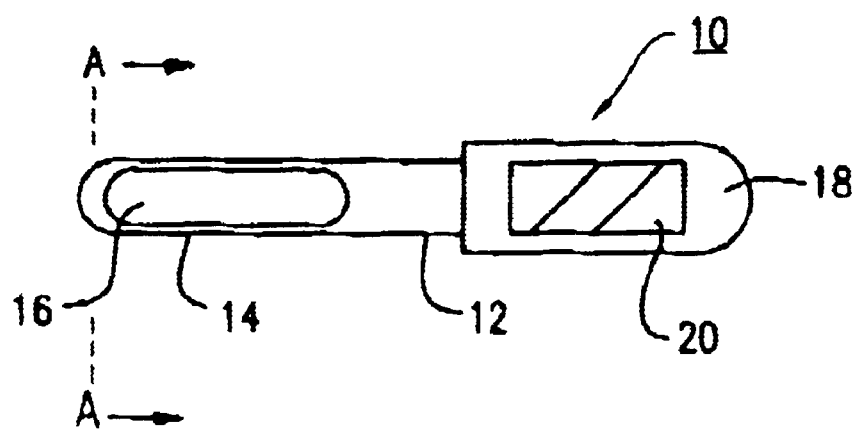
FIG. 1 is a plan view of one embodiment of the device of the present invention.
Figure 1A:
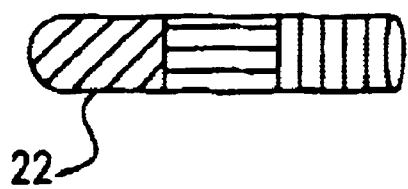
FIG. 1a depicts a cap which can cover the first portion of the reagent zone of the device.
Figure 2:
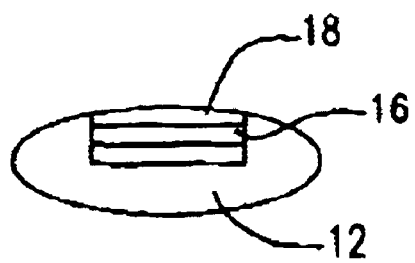
FIG. 2 is a view of the device shown in FIG. 1 taken through lines A–A'
Figure 3:
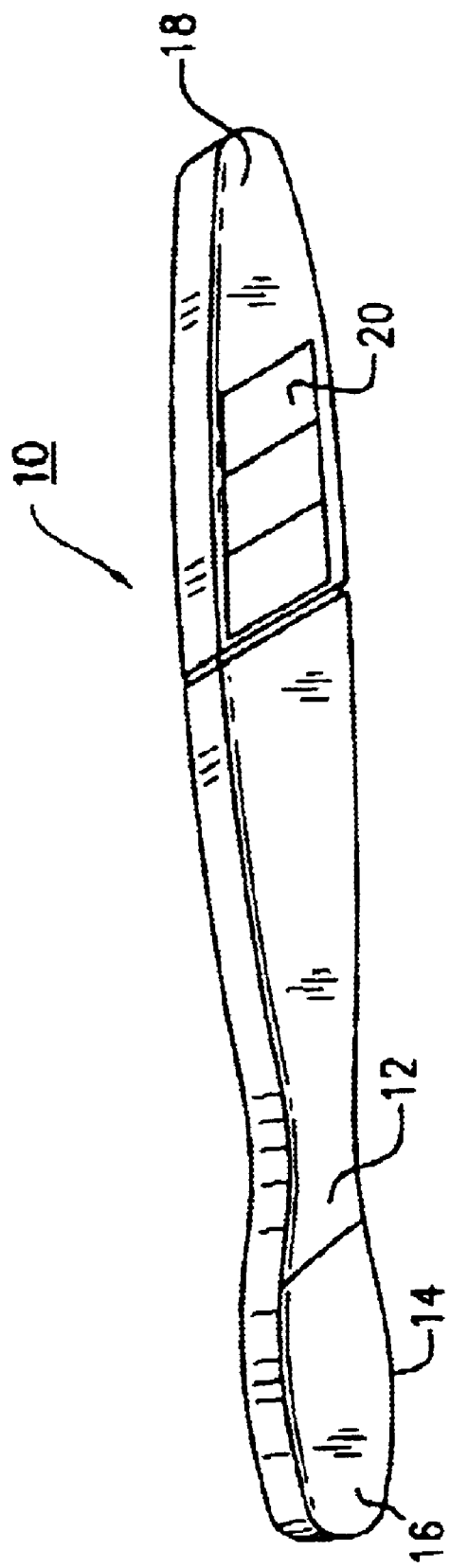
FIG. 3 is a view of another configuration of the device of the invention.

With reference to the Drawings, FIGS. 1–3, are representations of the device 10 of the present invention and depict the device as an elongated member 12 having a first portion thereof 14, containing the regent 16 and a second portion 18 which serves as a handle by which the person can hold the device. The cap 22, the cover or handle is where color chart 20 may be located for easy comparison to the reagent portion of the dipstick. The color chart can contain one or more inscriptions such as the specific gravity for each color or a designation whether the color represents normal hydration, moderate dehydration or a dehydration state that is dangerous, hazardous and requires immediate attention.

Both the specific gravity and the designations can be included if desired.

While FIGS. 1–3 depict two embodiments of this invention, several other configurations can also be employed In practice, however, having the device in the form similar to that of a dipstick is preferred. The only requirement is that the device be configured so that when it is held the urine stream of the person using the device can be easily directed onto the portion bearing the reagent and that the color chart 20 be in close proximity to the reagent for ease of color comparison.

The reagent employed in this invention for the determination of specific gravity, can be selected from a variety of color indicators which react with urine and provide a color change within the specific gravity ranges indicated above.

It is of course desirable that the reagent indicator reacts quickly with the urine and undergoes a color change so that the person will know whether he or she is dehydrated. Since urine provided during the test is above room temperature, that is at body temperature, the reaction and color formation may be proceed quicker than if the specimen were provided in a paper cup and not evaluated until after it had cooled to room temperature.

Hence, the only requirement of the reagent which is disposed on the device is that it provide a color change in response to the specific gravity ranges. The three colors should of course be distinct from one another.

In practice, the reagent can be composed of one component which changes color over each of the above (i)–(iii) specific gravity ranges. Alternatively, three separate reagents could be employed, each of which changes color only for one of the specific gravity ranges.

One reagent which has been found to be particularly useful in the present invention is comprised of bromthymol blue, poly(methylvinyl ether/maleic anhydride) and an alkaline compound such as sodium hydroxide.

A particular preferred reagent indicator is one composed of from about 2.8 weight percent of bromthymol blue, from about 68 weight percent of poly(methylvinyl ether/maleic anhydride), and from about 28.4 weight percent of sodium hydroxide.

Other indicator reagents can also be employed in this invention in place of the above as long as they exhibit visually detectable color changes which correspond to the aforementioned specific gravity ranges. Phenolphthalein, bromphenol blue and phenol red can also be used.

The device of the present invention can be fabricated from and contain a variety of products including plastic, metal and the like, or combinations thereof. In its most simple form and for economic reasons, the device is preferably made of plastic or any composite material composed of polyethylene, polypropylene or other similar substances. . Since the device is used only once and then disposed of, it is preferred to keep the cost per unit low. The reagent employed in the device can be affixed to the elongated member by a variety of methods. It can be absorbed on a porous membrane such as a woven matrix of cellulosic fibers or other substrate material which can retain the reagent and is itself affixed to the elongated member. The reagent can also be contained in a recessed section of the elongated member.

In preparing the device a variety of steps can be taken to minimize costs. For example, the elongated member can be molded or exuded from an inert plastic and the color chart affixed thereto as a decal or label or printed directly on the cap, cover or plastic handle 18. As indicated The reagent can be applied by impregnation of a porous substrate material which can be affixed to the first portion 12 of the device. Various other suitable techniques can also be employed to minimize the cost of the device.

Each device of this invention can be packaged in individual containers or covered with materials such as plastic film or metal foil, without a major increase in cost. If the particular choice of reagent should require that it be shielded from sunlight until used, then light-tight packaging would be preferred at least on the first portion 12 of the device.

It is evident from the above discussion that the device of the present invention is a desirable alternative, replacement and improvement for the test methods currently used.

Further, there is no need for a person to visit a laboratory, doctor's office or other facility to provide a specimen in a paper cup and deliver it to another person which, in some instances is somewhat embarrassing and most importantly time consuming.

With the availability of the device of this invention a person can merely visit a restroom or a semi-private area outdoors and urinate on the first portion of the device. The results are instantaneous and the hydration or dehydration status can immediately determined. If the person is dehydrated, medical or other action can be taken immediately without the necessity to await laboratory results.

As indicated above, the device of the present invention finds use in a variety of areas and provides a simple, fast and accurate determination of the hydration state of a person. The device is particularly useful in numerous sports activities wherein overexertion can result in the participant becoming dehydrated without awareness of his or her condition until the person's condition might reach a dangerous state. For example, in professional sports there is a highly publicized need to protect professional athletes from injury or death from unrecognized dehydration especially in outdoor sports involving heat exposure and high-intensity exercise.

The testing of such athletes is enforced by professional sports organizations and the device of the present invention provides a quick and easy method for testing. Also, professional, college and high school athletes should be tested since many athletes consider themselves to be in excellent physical condition and can extend themselves unknowingly beyond their capabilities, and become dehydrated without being aware of their condition and require immediate medical attention, if necessary. The same problem can occur with elementary school sports, scholastic sports organizations, and other groups such as little league, professional and pee wee football, soccer and the like.

Even amateur or other activities, such as running, bicycling, hiking, and the like, can benefit the use and availability of the present device.

Other activities for which the device of this invention can be employed include but are not limited to, fitness studios, gyms, health clubs, martial art studios, dance studios, and the like. Many outdoor activities can also benefit by the simple and quick use of the dehydration device of this invention such as members of the military who are stationed in hot environments where dehydration unchecked can have serious consequences. Additionally, construction workers, police, firemen, rescue workers, as well as those who visit the beaches, parks and outdoors in hot weather.

A unique aspect of the device of the present invention, is that its use is essentially independent of the outside atmospheric temperature. It is well known that chemical reactions are usually dependent on temperature; the lower the temperature, the slower the chemical reaction. Hence a chemical reaction such as between urine and a color indicator would be expected to proceed much slower in cold weather than at room temperature. For instance, in cold weather sport, such as hockey, football, skiing, ice skating, and the like, the urine stream of one using the device of the present invention outdoors would be warm, that is, at body temperature and hence the chemical reaction, such as that which would occur between a specimen and a color indicator, would proceed much quicker than if the specimen were at room or the outdoor temperature. Thus, if the color indicator was not very sensitive, the temperature of the urine specimen would enhance the chemical reaction and the test results.

Although the invention has been illustrated by the aforementioned disclosure, It is not to be construed as being limited to material employed therein, but rather the invention relates to the generic area as hereinbefore disclosed. Various modifications and embodiments can be made without departing from the spirit and scope thereof.

What is claimed is:

1. An article for the qualitative determination of dehydration in a human comprising a compact, portable, plastic, hand-held device having an elongated member, said member being comprised of:
   (a) at a first lower portion thereof, a zone containing at least one dry chemical reagent, which when contacted with a specimen of human urine exhibits a different, specific color corresponding to whether the specific gravity of urine is within the individual ranges of:
      (i) less than about 1.015,
      (ii) between about 1.105 and about 1.025,
      (iii) greater than about 1.025
   (b) affixed at a second upper portion thereof, a zone of predetermined separate colors, each of which color is indicative of an individual specific gravity range and therefore the hydration status of said human, and wherein the device is so configured that a person can hold the device and urinated directly onto the first lower portion thereof without urine contacting the remainder of the device and wherein a color change of the chemical reagent produced by contact with the urine can immediately and privately be compared with the colors affixed to the second upper portion, of the article.

2. The device of claim 1 wherein the elongated member is composed of polyethylene plastic.

3. The device of claim 1 wherein the elongated member is composed of polypropylene plastic.

4. The device of claim 1 wherein the elongated member is approximately the size of a medical torgue depressor.

5. The device of claim 1 wherein the chemical indicator zone is comprised of a mixture of chemicals, which, when contacted with urine, will produce different colors corresponding to the specific gravity of a particular urine specimen.

6. The device of claim 2 wherein the chemical indicator when contacted with urine exhibits a green color for a urine specific gravity of less than about 1.015; a speckled green-yellow color for a urine specific gravity of between about 1.015 and about 1.025; and a yellow color for urine specific gravity of greater than about 1.025.

7. The device of claim 6 wherein the chemical indicator is a mixture of bromthymol blue, poly(methylvinyl ether/maleic anhydride) and sodium hydroxide.

8. The device of claim 7 wherein the chemical indicator is a mixture of:
   (a) about 2.8 weight percent of bromthymol blue
   (b) about 68.8 weight percent of poly(methylvinyl ether/maleic anhydride)
   (c) about 28.4 weight percent of sodium hydroxide.

9. The device of claim 6 wherein the same colors are also set forth on at least one of the cap, or cover of the device with a designation of the specific gravity for each color.

10. The device of claim 6 wherein the same colors are set forth on the second portion thereof with a designation of normal hydration for green, moderate hydration for the speckled green-yellow and dehydration for the yellow color.

11. The device of claim 6 wherein under each color both the specific gravity and the hydration designations are indicated.

12. The device of claim 1 which is encapsulated with a removable and environmentally disposable moisture proof covering.

13. The device of claim 12 wherein the moisture proof covering is composed of plastic.

14. The device of claim 12 wherein the moisture proof covering is composed of foil.

15. The device of claim 14 wherein the foil is aluminum.

16. A process for the self-determination of the hydration state of a human which comprises said human in private urinating directly onto the first portion of the device of claim 1 and comparing the color change produced by the contact of the chemical substrate with urine, with the colors indicated on the cap, cover or second portion of said device.

* * * * *

UNITED STATES PATENT AND TRADEMARK OFFICE
CERTIFICATE OF CORRECTION

| | |
|---|---|
| PATENT NO. | : 6,750,007 B2 |
| APPLICATION NO. | : 10/092656 |
| DATED | : June 15, 2004 |
| INVENTOR(S) | : Nelson Canter and Susan Pannullo |

It is certified that error appears in the above-identified patent and that said Letters Patent is hereby corrected as shown below:

In the Claims

Column 5, line 32, "1.105" should be --1.015--.

Column 5, line 39, "urinated" should be --urinate--.

Signed and Sealed this
Sixteenth Day of July, 2013

Teresa Stanek Rea
*Acting Director of the United States Patent and Trademark Office*